(12) United States Patent
Hori et al.

(10) Patent No.: US 6,916,657 B2
(45) Date of Patent: Jul. 12, 2005

(54) EVALUATION METHOD FOR POLYCRYSTALLINE SILICON

(75) Inventors: Kenji Hori, Tokyo (JP); Go Sasaki, Yokkaichi (JP)

(73) Assignees: Mitsubishi Materials Silicon Corporation, Tokyo (JP); Mitsubishi Materials Polycrystalline Silicon Corporation, Yokkaichi (JP)

( * ) Notice: Subject to any disclaimer, the term of this patent is extended or adjusted under 35 U.S.C. 154(b) by 342 days.

(21) Appl. No.: 09/867,418

(22) Filed: May 31, 2001

(65) Prior Publication Data

US 2002/0000186 A1 Jan. 3, 2002

(30) Foreign Application Priority Data

Jun. 26, 2000 (JP) ..................................... P2000-191744

(51) Int. Cl.⁷ ........................... G01N 23/083; G01T 1/00
(52) U.S. Cl. ................. 436/4; 436/5; 438/14; 117/2
(58) Field of Search ................. 436/4–5, 177, 436/164; 117/2, 201; 438/14

(56) References Cited

U.S. PATENT DOCUMENTS

| | | | |
|---|---|---|---|
| 4,213,937 A | * 7/1980 | Padovani et al. | 422/142 |
| 5,793,833 A | 8/1998 | Imai | |
| 6,066,872 A | * 5/2000 | Okada et al. | 257/309 |
| 6,172,376 B1 | 1/2001 | Xu et al. | 250/574 |
| 6,429,035 B2 | * 8/2002 | Nakagawa et al. | 438/57 |
| 6,534,353 B1 | * 3/2003 | Kuramasu et al. | 438/197 |

FOREIGN PATENT DOCUMENTS

| | | | |
|---|---|---|---|
| EP | 0390671 A2 | | 10/1990 |
| JP | 5-319990 | | 12/1993 |
| JP | 6-283498 | | 10/1994 |
| JP | 8-48512 | | 2/1996 |
| JP | 11-145230 | * | 5/1999 |
| JP | 11-171685 | | 6/1999 |
| JP | 2000-128692 | | 5/2000 |

OTHER PUBLICATIONS

Chen et al., "Simultaneous Determation of Fe, Al, Ca, B, As and P in Industrial Silicon or Multi–crystal Silicon by ICP–AES," Yunnan Metallurgy, Jul., 1998, abstract only.

* cited by examiner

*Primary Examiner*—Lyle A. Alexander
(74) *Attorney, Agent, or Firm*—Pillsbury Winthrop Shaw Pittman LLP

(57) ABSTRACT

An evaluation method for polycrystalline silicon including the steps of immersing the polycrystalline silicon in an agent which is capable of dissolving the polycrystalline silicon, and counting the number of foreign particles in the agent. The polycrystalline silicon thus evaluated may be used as a material for pulling single crystal silicon. The evaluation method may further include a step of analyzing the composition of the foreign particles. In yet another aspect, the evaluation method may further include a step of subjecting the agent to a circulation filtering process prior to the immersion of the polycrystalline silicon in the agent.

14 Claims, 3 Drawing Sheets

EVALUATION METHOD FOR POLYCRYSTALLINE SILICON

BACKGROUND OF THE INVENTION

1. Field of the Invention

The present invention relates to an evaluation method for polycrystalline silicon. More specifically, the present invention relates to an evaluation method for polycrystalline silicon which may be used as a material for pulling single crystal silicon.

2. Description of Related Art

As a method for producing single crystal silicon, the Czochralski method (hereinafter referred to as the CZ method) is well-known. The CZ method has the advantages that single crystals of a large diameter and high purity can easily be obtained with no transition state or a small number of little lattice defects.

In the CZ method, after washing a polycrystalline silicon piece of extremely high purity, the polycrystalline silicon piece is put into a quartz crucible and melted in a heating furnace. At that time a necessary amount of a conductive impurity (e.g., an additive or a dopant) is added to control, for example, the type of crystal to be prepared. For instance, a P-type crystal is obtained if boron (B) is added whereas an N-type crystal is obtained if phosphorus (P) or antimony (Sb) is added. Also, the resistivity of the crystal may be controlled by changing the amount of the conductive impurity added.

After that, a seed crystal (a single crystal) which is hung by a wire is immersed in the melted silicon and the single crystal is grown by gradually pulling the wire while rotating the single crystal. Single crystal silicon having various diameters and characteristics may be produced by controlling the temperature, the pulling speed and so forth. The crystal grown in this manner becomes a perfect single crystal. The lower the amount of contaminants contained in the polycrystalline silicon used as the material, the less likely that the single crystal produced is subjected to a transition.

However, even if the purity of the polycrystalline silicon is extremely high at first, contaminants, such as metal particles, may attach to the surface of silicon when the polycrystalline silicon is crushed into pieces having a certain particle size. Also, a fine resin particle may attach to the surface of the polycrystalline silicon while being transported. Accordingly, there are cases where fine particles of a metal or a resin are already attached to the surface of polycrystalline silicon pieces when, for instance, a manufacturer of single crystal silicon purchases the polycrystalline silicon from a supplier. For this reason, although the manufacturer washes the polycrystalline silicon beforehand, not all of the contaminants are washed away and some may still remain on the surface.

Since the contaminants attached to the surface of polycrystalline silicon pieces may cause problems, such as crystal defects, in single crystal silicon prepared by the pulling method, it is naturally required to use as clean a polycrystalline silicon piece as possible. However, because the number of particles of contaminants attached to the surface of polycrystalline silicon differ depending on the supplier or product lot, it is necessary to determine the number of particles attached to the polycrystalline silicon before its use, so that it becomes possible to select usable polycrystalline silicon, or use the polycrystalline silicon for a suitable purpose.

Conventionally, the evaluation of the quality of polycrystalline silicon has been carried out by actually preparing single crystal silicon from purchased polycrystalline silicon and measuring, for instance, the density of defects, such as crystal defects, of the single crystal silicon obtained. Accordingly, it takes time to carry out the evaluation procedure and it is difficult to flexibly apply the evaluation results to actual practice, such as the above-mentioned selection of polycrystalline silicon or use for a suitable purpose.

The present invention was achieved in consideration of the above problems and its objectives include providing a method for effectively evaluating the level of contaminants contained in polycrystalline silicon which may be used as a material.

SUMMARY OF THE INVENTION

The present invention provides an evaluation method for polycrystalline silicon including the steps of immersing the polycrystalline silicon in an agent which is capable of dissolving the polycrystalline silicon, and counting the number of foreign particles in the agent.

In accordance with another aspect of the invention, the polycrystalline silicon is used as a material for pulling single crystal silicon.

In yet another aspect of the invention, the polycrystalline silicon immersed in the agent is aggregated or in pellet shape.

According to the evaluation method for polycrystalline silicon, when the polycrystalline silicon of aggregated or pellet shape is immersed in the agent, the surface of the polycrystalline silicon is dissolved and foreign matter attached to or contained in the polycrystalline silicon is dispersed in the agent. Accordingly, a part of the agent which contains the foreign matter may be taken as a sample and the number of the foreign matter particles in the sample may be counted by using such a measuring device as a particle counter.

According to the above evaluation method of the present invention, the amount of foreign matter contained in polycrystalline silicon may be predetermined without actually pulling a single crystal from it. Thus, the evaluation results may be more rapidly used in practice as compared with a conventional technique and, for instance, it becomes easy to select polycrystalline silicon to be used as a material for pulling single crystals, or to use the polycrystalline silicon for a suitable application.

In yet another aspect of the invention, the evaluation method further includes a step of analyzing the composition of the foreign particles.

According to the above evaluation method for polycrystalline silicon, not only the evaluation of the particle number but also the determination of the kind or origin of the particles may be carried out. Hence, clues for the cause of the attachment of the foreign matter to the polycrystalline silicon may be obtained. Accordingly, if the cause is detected, it may become possible to obtain clean polycrystalline silicon which is not contaminated by the foreign matter by taking appropriate precautions.

In yet another aspect of the invention, the evaluation method further includes a step of subjecting the agent to a circulation filtering process prior to the immersion of the polycrystalline silicon in the agent.

According to the above evaluation method for polycrystalline silicon, since the agent is subjected to the circulation filtering process prior to the immersion of the polycrystalline silicon in the agent, it is possible to maintain the agent in a clean state and, hence, the number of foreign particles in the agent may be accurately counted.

BRIEF DESCRIPTION OF THE DRAWINGS

Some of the features and advantages of the invention have been described, and others will become apparent from the detailed description which follows and from the accompanying drawings, in which.

DETAILED DESCRIPTION OF THE INVENTION

The invention summarized above and defined by the enumerated claims may be better understood by referring to the following detailed description, which should be read with reference to the accompanying drawings. This detailed description of a particular preferred embodiment, set out below to enable one to build and use one particular implementation of the invention, is not intended to limit the enumerated claims, but to serve as a particular example thereof.

An evaluation method for polycrystalline silicon according to an embodiment of the present invention will be described with reference to FIGS. 1A through 1D.

Figure 1A:
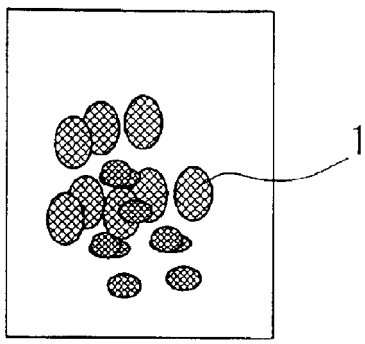
FIGS. 1A to 1D are diagrams for explaining an evaluation method for polycrystalline silicon according to an embodiment of the present invention.

First, as shown in FIG. 1A, a certain amount (for instance, 5 kg) of polycrystalline silicon pieces 1 to be evaluated are prepared. The shape of the polycrystalline silicon pieces 1 is not particularly limited and they may be aggregated or pellet shaped.

Figure 1B:
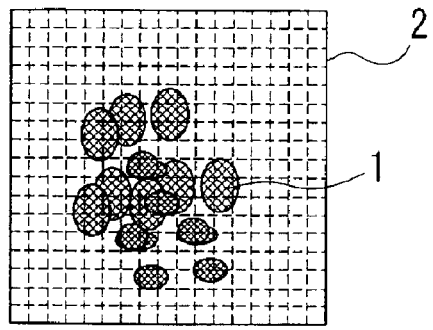

Then, as shown in FIG. 1B, the polycrystalline silicon pieces 1 are put into a container 2 made of, for instance, polyethylene or polytetrafluoroethylene. Since the container 2 is immersed in an etchant in the next step, it is necessary to use a material having a resistance to the etchant for the container 2.

Figure 1C:
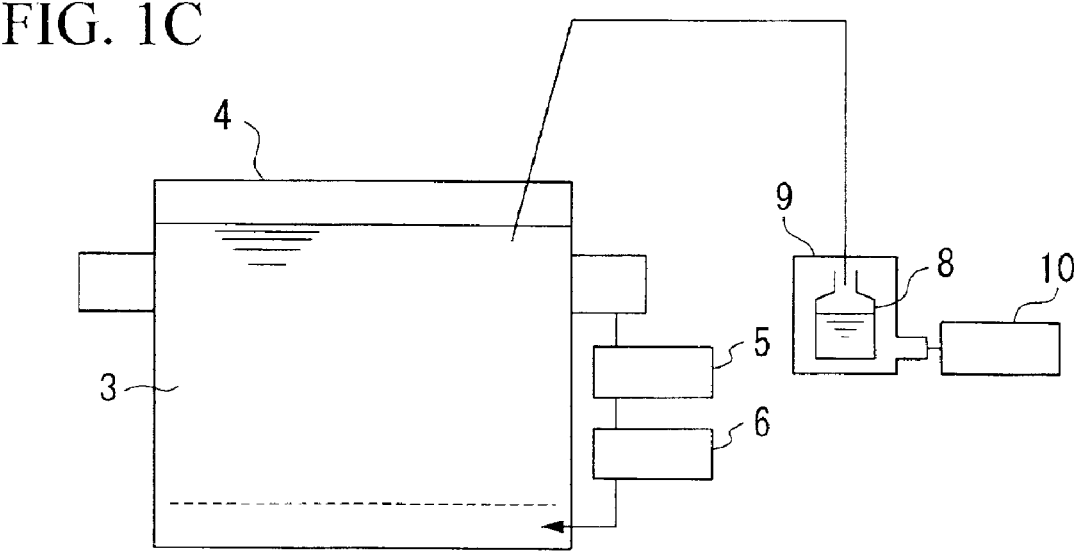
Figure 1D:
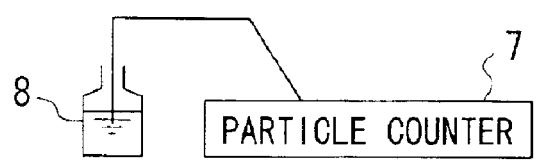

After that, as shown in FIG. 1C, the container 2, in which the above-mentioned polycrystalline silicon pieces 1 are placed, is immersed in an etchant 3 contained in an etching vessel 4. The kind of etchant 3 used in this embodiment is not particularly limited as long as it is capable of dissolving the polycrystalline silicon pieces 1. Examples of such an etchant include hydrofluoric and nitric acids. Note that the etching vessel 4 used in this embodiment is provided with circulation filtering equipment, such as a pump 5 or a filter 6, so that the etchant 3 may be filtered by circulation to reach a particle free state before the container 2 is immersed in the etchant 3.

Next, the circulation filtering process is stopped and, after the container 2 is put into and taken out of the etching vessel 4 a few times, the container 2 is pulled out from the etching vessel 4. After that a portion of the etchant 3 is taken as a sample by using an arbitrary container 8 made of, for instance, polyethylene or polytetrafluoroethylene. At that time, fine particles or a powder of polycrystalline silicon are contained in the sampled etchant. As a method for taking the sample of the etchant 3, the container 8 may be placed in a sealed chamber 9, and the chamber 9 evacuated by using a vacuum pump 10 so that the sample of the etchant 3 is drawn into the container 8 as shown in FIG. 1C (i.e., a clean sampling method).

The collected sample solution is left for a certain period (e.g., a couple of days) so that all of the fine particles or powder of the polycrystalline silicon are dissolved in the solution, and then the number of particles of foreign matter in the sample solution per unit volume is measured by using a particle counter 7. Since the fine particles or powder of the polycrystalline silicon have been dissolved in the solution, only the particles of foreign matter attached to or contained in the polycrystalline silicon are counted. By using this counting method, it becomes possible to improve the efficiency of the measurement.

In addition, the composition of the foreign particles may be analyzed by using such methods as Scanning Electron Microscopy (SEM), or Energy Dispersive X-ray spectroscopy (EDX). By using such analytical methods, not only the evaluation of the particle number but also the determination of the kind or origin of the particles may be carried out. Accordingly, the composition of the particles may be detected as, for instance, alumina, carbon, a vinyl chloride type resin, a polyethylene type resin, a polytetrafluoroethylene type resin, or a hard metal.

Figure 2A:
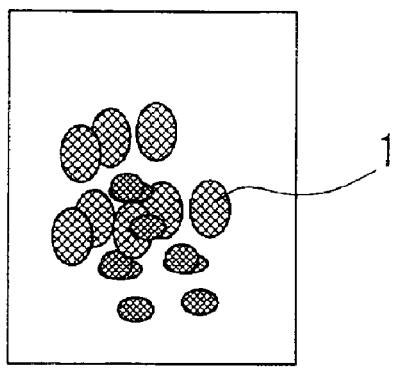
FIGS. 2A to 2C are diagrams for explaining an evaluation method for polycrystalline silicon according to another embodiment of the present invention.
Figure 2B:
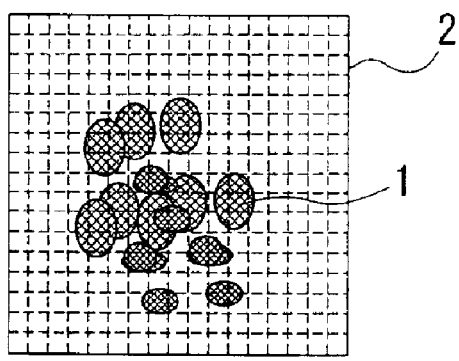
Figure 2C:
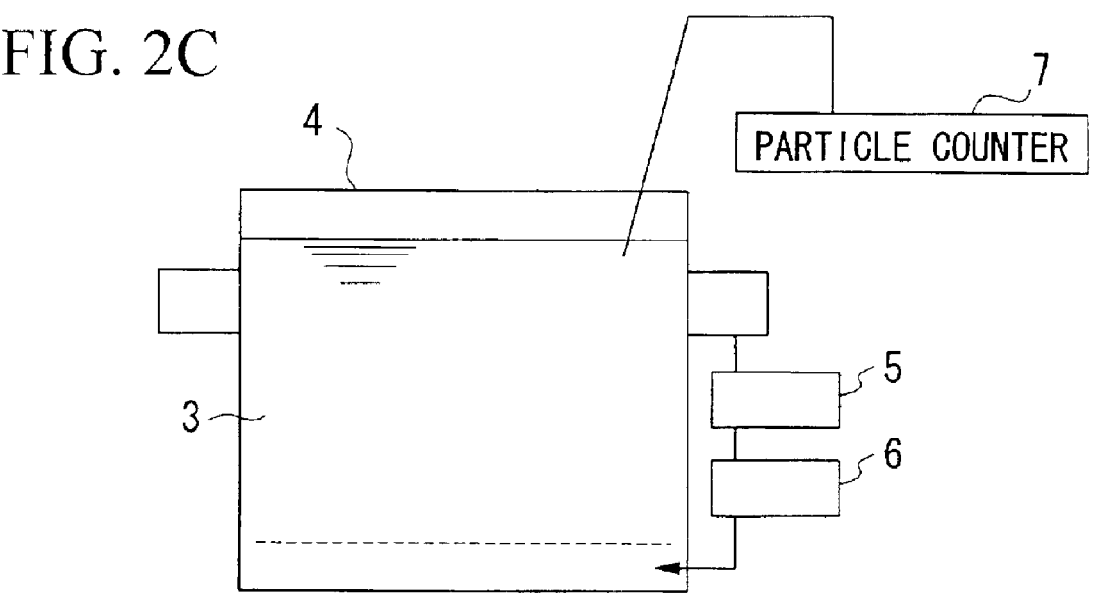

It is also possible to directly measure the etchant 3 in the etching vessel 4 by using the particle counter 7 as shown in FIG. 2C, after immersing the container 2, in which the polycrystalline silicon pieces I are placed, into the etchant 3 in the etching vessel 4 as shown in FIGS. 2A and 2B and allowing to stand for a certain period in the same manner as described above.

According to the embodiment of the present invention, as mentioned above, the amount of foreign matter contained in polycrystalline silicon may be predetermined without actually pulling a single crystal from it. Accordingly, by using the evaluation method of the present invention, the evaluation result may be more rapidly used in practice as compared with a conventional technique and, for instance, it becomes easy to select polycrystalline silicon to be used as a material for pulling single crystals, or to use the polycrystalline silicon for a suitable application.

Also, if the analysis of components of foreign matter is conducted, clues for the cause of attachment of the foreign matter to the polycrystalline silicon may be obtained. Accordingly, if the cause is detected, it may become possible to obtain clean polycrystalline silicon which is not contaminated by foreign matter. Moreover, according to the embodiment of the present invention, since the etchant 3 is subjected to the circulation filtering process prior to the immersion of the polycrystalline silicon pieces I in the etchant 3, it is possible to maintain the etchant 3 in a clean state and, hence, the number of foreign particles in the etchant 3 can be accurately counted.

Note that the scope of the present invention is not limited to the above-described embodiment and various alterations, modifications, and improvements may be made within the sprit and scope of the invention. For example, although hydrofluoric and nitric acids are used as the etchant 3 in the above embodiment, other agents may be employed as the etchant 3 as long as the agent is capable of etching polycrystalline silicon. Also, such factors as the configuration of the etching vessel 4 or a concrete evaluation manner are not limited and any suitable adjustments may be made thereto.

Next, evaluation data which was actually obtained by using the method according to the embodiment of the present invention will be explained.

Figure 3:
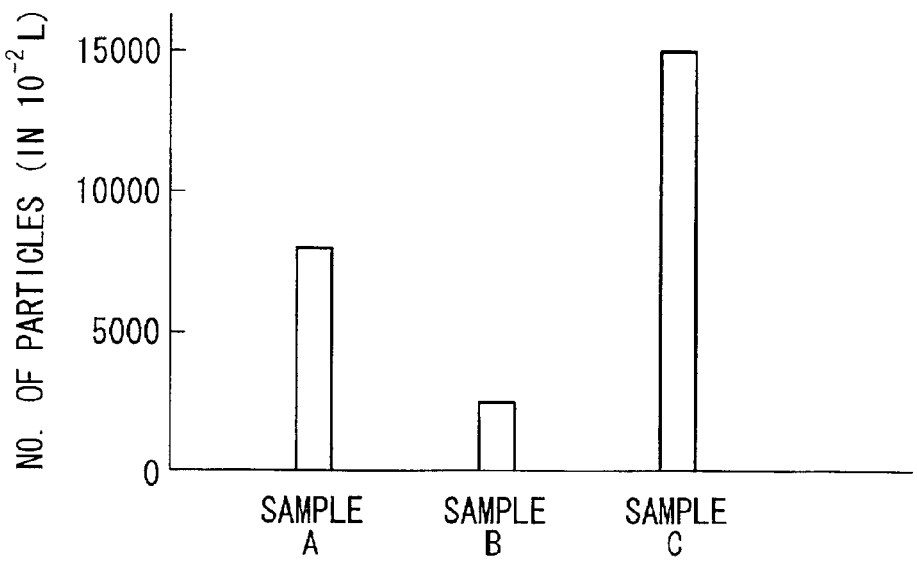
FIG. 3 is a graph showing the results of measuring the number of particles contained in each sample in accordance with the embodiment of the present invention.

Three kinds of samples (A, B and C) of polycrystalline silicon were prepared as evaluation objects. The number of particles contained in each sample counted in accordance with the method described in the above embodiment are shown in FIG. 3. The particle counter used is capable of counting the number of particles in accordance with particle size and in this case the comparison was made within a particle size range of between 0.2 and 5 µm. As shown in FIG. 3, the number of particles contained in samples A–C of $1 \times 10^{-2}$ L was 8,000 for the sample A; 2,500 for the sample B; and 15,000 for the sample C.

Figure 4:
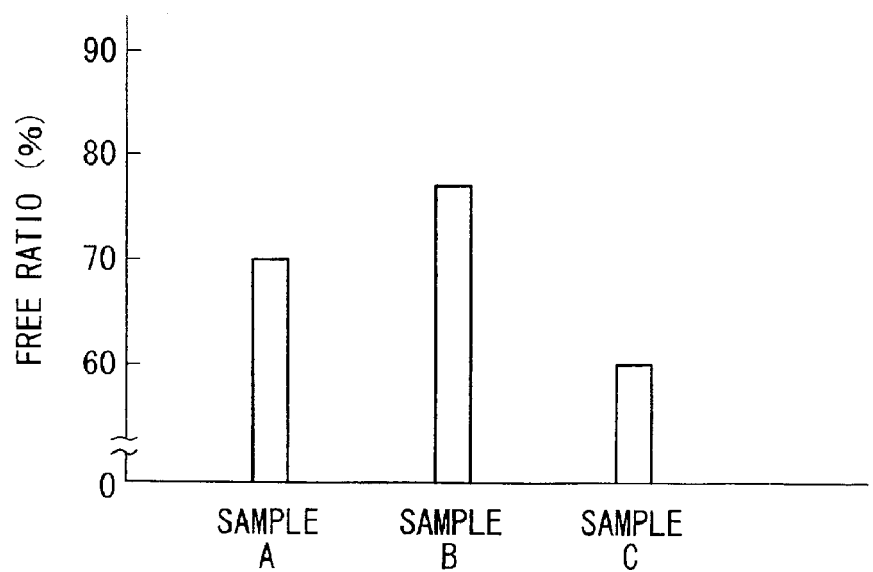
FIG. 4 is a graph showing the results of measuring the free ratio of each single crystal silicon obtained from polycrystalline silicon corresponding to the respective sample described in FIG. 3.

On the other hand, polycrystalline silicon pieces corresponding to the samples A, B, and C, respectively, were used as the material and the pulling method was actually carried out to measure the free ratio of each single crystal silicon prepared. The results are shown in FIG. 4. The free ratio of the single crystal silicon samples A–C per unit volume is 70% for the sample A, 77% for the sample B, and 60% for the sample C. Note that the term "free ratio" means the ratio of no transition single crystals.

That is, it was confirmed that the number of particles in each of the samples A–C corresponds to the free ratio (defect density) in the single crystal silicon prepared. Accordingly, it is demonstrated that polycrystalline silicon may be assuredly evaluated by using the method according to the present invention.

Having thus described an exemplary embodiment of the invention, it will be apparent that various alterations, modifications, and improvements will readily occur to those skilled in the art. Such alterations, modifications, and improvements, though not expressly described above, are nonetheless intended and implied to be within the spirit and scope of the invention. Accordingly, the foregoing discussion is intended to be illustrative only: the invention is limited and defined only by the following claims and equivalents thereto.

What is claimed is:

1. An evaluation method for polycrystalline silicon which is used as a material for pulling single crystal silicon, comprising the steps of:

immersing a predetermined amount of the polycrystalline silicon in a predetermined amount of an etchant contained in a vessel, which etchant is capable of dissolving the polycrystalline silicon allowing at least a part of the polycrystalline silicon at a surface thereof to dissolve in the etchant; and using a particle counter to count the number of foreign particles dispersed in the etchant to determine the quality of the polycrystalline silicon based on the number of foreign particle counted.

2. An evaluation method for polycrystalline silicon as set forth in claim 1, wherein the polycrystalline silicon immersed in the etchant is aggregated or in pellet shape.

3. An evaluation method for polycrystalline silicon as set forth in claim 1, further comprising the step of:

analyzing the composition of the foreign particles.

4. An evaluation method for polycrystalline silicon as set forth in claim 1, wherein said foreign particles cause crystal defects.

5. An evaluation method for polycrystalline silicon as set forth in claim 3, wherein the analysis is carried out using scanning electron microscopy or energy dispersive X-ray spectroscopy.

6. An evaluation method for polycrystalline silicon as set forth in claim 1, further comprising the step of:

subjecting the etchant to a circulation filtering process prior to the immersion of the polycrystalline silicon in the agent.

7. An evaluation method for polycrystalline silicon as set forth in claim 2, further comprising the step of:

subjecting the etchant to a circulation filtering process prior to the immersion of the polycrystalline silicon in the etchant.

8. An evaluation method for polycrystalline silicon as set forth in claim 3, further comprising the step of:

subjecting the etchant to a circulation filtering process prior to the immersion of the polycrystalline silicon in the etchant.

9. An evaluation method for polycrystalline silicon as set forth in claim 4, further comprising the step of: subjecting the etchant to a circulation filtering process prior to the immersion of the polycrystalline silicon in the etchant.

10. An evaluation method for polycrystalline silicon as set forth in claim 5, further comprising the step of:

subjecting the etchant to a circulation filtering process prior to the immersion of the polycrystalline silicon in the etchant.

11. An evaluation method for polycrystalline silicon as set forth in claim 1, wherein the etchant is hydrofluoric acid or nitric acid.

12. An evaluation method according to claim 1, wherein the etchant having the polycrystalline silicon dissolved therein is a liquid when the particle counter is placed therein.

13. An evaluation method according to claim 1, further comprising the step of:

determining the kind or origin of the foreign particles.

14. An evaluation method according to claim 1, wherein the foreign particles are attached to or contained in the polycrystalline silicon.

* * * * *